United States Patent [19]
Loubser

[11] Patent Number: 6,110,139
[45] Date of Patent: Aug. 29, 2000

[54] RETROGRADE PERFUSION MONITORING AND CONTROL SYSTEM

[76] Inventor: Paul Gerhard Loubser, 302 Lakeglen Ct., Sugarland, Tex. 77478

[21] Appl. No.: 08/955,325

[22] Filed: Oct. 21, 1997

[51] Int. Cl.$^7$ .................................................. A61M 1/00
[52] U.S. Cl. .................................................. 604/30; 604/4
[58] Field of Search .................................. 600/486, 505, 600/485, 561; 422/46, 45; 604/4, 30

[56] References Cited

U.S. PATENT DOCUMENTS

| | | |
|---|---|---|
| 4,378,797 | 4/1983 | Osterholm . |
| 4,393,863 | 7/1983 | Osterholm . |
| 4,424,814 | 1/1984 | Secunda . |
| 4,445,500 | 5/1984 | Osterholm . |
| 4,445,514 | 5/1984 | Osterholm . |
| 4,445,886 | 5/1984 | Osterholm . |
| 4,445,887 | 5/1984 | Osterholm . |
| 4,445,888 | 5/1984 | Osterholm . |
| 4,446,154 | 5/1984 | Osterholm . |
| 4,446,155 | 5/1984 | Osterholm . |
| 4,450,841 | 5/1984 | Osterholm . |
| 4,451,251 | 5/1984 | Osterholm . |
| 4,686,085 | 8/1987 | Osterholm . |
| 4,688,577 | 8/1987 | Bro ........................................ 128/670 |
| 4,739,771 | 4/1988 | Manwaring . |
| 4,750,493 | 6/1988 | Brader . |
| 4,758,431 | 7/1988 | Osterholm . |
| 4,830,849 | 5/1989 | Osterholm . |
| 4,840,617 | 6/1989 | Osterholm . |
| 4,920,963 | 5/1990 | Brader . |
| 5,011,468 | 4/1991 | Lundquist et al. . |
| 5,011,469 | 4/1991 | Buckberg et al. . |
| 5,295,995 | 3/1994 | Kleiman . |
| 5,391,142 | 2/1995 | Sites et al. ................................. 604/4 |
| 5,456,703 | 10/1995 | Beeuwkes . |
| 5,474,533 | 12/1995 | Ward et al. . |
| 5,513,637 | 5/1996 | Twiss et al. . |
| 5,521,215 | 5/1996 | Mechoulam et al. . |
| 5,525,621 | 6/1996 | Burt et al. . |
| 5,579,774 | 12/1996 | Miller et al. ........................... 128/667 |
| 5,769,812 | 6/1998 | Stevens et al. ........................... 604/4 |

FOREIGN PATENT DOCUMENTS

WO 95/23620   9/1995   WIPO .

OTHER PUBLICATIONS

Boeckxstaens and Flameng, Retrograde Cerebral Perfusion Does Not Perfuse the Brain in Nonhuman Primates, Ann Thorac Surg. 1995, pp.319–328, vol. 60.

Chanyl, "Cerebral Perfusion and Hypothermic Circulatory Arrest", Journal of Cardiothoracic and Vascular Anesthesia, Jan. 1996, pp. 75–82, vol. 10, No. 1.

deBrux Et Al, Retrograde Cerbral Perfusion: Anatomic Study of the Distribution of Blood to the Brain, Ann Thorac Surg. 1995, pp. 1294–1298, vol. 60.

Deeb Et Al, "Retrograde Cerebral Perfusion During Hypothermic Circulatory Arrest Reduces Neurologic Morbidity", The Journal of Thoracic and Cardiovascular Surgery, Feb. 1995, pp. 259–268, vol. 109, No. 2.

Dresser and McKinney, "Anatomic and Pathophysiologic Studies of the Human Internal Jugular Valve", The American Journal of Surgery, Aug. 1987, pp. 220–224, vol. 154.

(List continued on next page.)

Primary Examiner—Wynn Wood Coggins
Assistant Examiner—Deborah Blyveis
Attorney, Agent, or Firm—Sue Z. Shaper; Felsman, Bradley, Vaden, Gunter & Dillon

[57] ABSTRACT

Apparatus and methods for performing retrograde perfusion, especially during cardiopulmonary bypass operations, including dedicated pediatric scaled apparatus for retrograde perfusion of an adult human organ, organ system, or limb, especially the brain, employing small scale oxygenators and heat exchangers such as are designed for pediatric surgery; also including methods and apparatus for retrograde cerebral perfusion, using nonselective infravalvular cannulation of the superior vena cava, estimating the efficacy of cerebral perfusion by monitoring fluid flow across a valve of an internal jugular vein, modification of inflow pressure and administration of pharmacologic agents, and increasing fluid flow into a brain by occlusion of an inferior vena cava distal to its junction with an azygos vein.

24 Claims, 6 Drawing Sheets

OTHER PUBLICATIONS

Fisher Et Al, "Determinants and Clinical Significance of Jugular Venous Valve Competence", Circulation, Jan. 1982, pp. 188–196, vol. 65, No. 1.

Gottlob and May, "Venous Valves", 1986, pp. 16–17, Springer–Verlag, New York.

Grants Atlas of Anatomy, pp. 44,51,64,70.

Gravlee Et Al, "Cardiopulmonary Bypass Principles and Practice", 1993, pp. 39–45, Section 1, pp. 603–668, Section V, Williams & Wilkins, Baltimore.

Gray, "Anatomy of The Human Body", pp. 738 & 841, Lea & Febiger, Philadelphia.

Hessel, "Cardiopulmonary Bypass Circuitry and Cannulation Techniques", pp. 55–92, Section 1.

Imai Et Al, "Valve Injury: A New Complication of Internal Juglular Vein Cannulation", Aneasth Analg, 1994, pp. 1041–1046, vol. 78.

Imamaki Et Al, "Retrograde Cerebral Perfusion with Hypothermic Blood Provides Efficient Protection of the Brain: A Neuropathological Study", J. Card Surg, 1995, pp. 325–333, vol. 10.

Kitamura Et Al, "Operation for Type A Aortic Dissection: Introduction of Retrograde Cerebral Perfusion", Ann Thorac Surg, 1995, pp. 1195–1199, vol. 59.

Matalanis and Buxton, "Retrograde vital Organ Perfusion During Aortic Arch Repair", Ann Thrac Surg, Apr. 1993, pp.981–984, vol. 56.

Murase Et Al, "Continuous Retrograde Cerebral Perfusion for Protection of the Brain During Aortic Arch Surgery", Eur J Cardio–thorac Surg, Jul. 1993, pp. 597–600, vol. 7.

Okamoto Et Al, "How To Do It Selective Jugular Cannulation", Ann Thorac Surg, 1993, pp. 539, pp. 539, vol. 55.

Oohara Et Al, "Regional Cerebral Tissue Blood Flow Measured by Colored Microsphere Method During Retrograde Cerebral Perfusion", The Journal of Thoracic and Cardiovascular Surery, 1995, pp. 772–779, vol. 109, No. 4.

Pagano Et Al, "Retrograde Cerbral Perfusion: Clinical Experience in Emergency and Elective Aortic Operations", Ann Thorac Surg, 1995, pp.393–397, vol. 59.

Rao Et Al, "Retrograde Abdominal Visceral Perfusion: Is It Beneficial", Ann Thorac Surg, Jul. 1995, vol. 60.

Raskin and Coselli, Retrograde Cerebral Perfusion: Overview, Techniques and Results, Perfusion, 1995, pp. 51–57, vol. 10.

Schwartz and Hensley, "Continuous Retrograde Cerebral Perfusion as an Adjunct to Brain Protection During Deep Hypothermic Systemic Circulatory Arrest", Journal of Cardiothoracic and Vascular Anesthesia, Apr. 1995, pp. 205–214, vol. 9, No. 2.

Shepherd and Vanhoutte, "Veins and their Control", 1975, pp. 171–179, W.B. Saunders Company, London.

Takamoto Et Al, "Simple Hypothermic Retrograde Cerebral Perfusion During Aortic Arch Surgery", J. Cardiovasc Surg, Feb. 1992, pp. 580–587, vol. 33.

Tsuchida Et Al, "Cerebral Death–Like Conditions After Aortic Aneurysm Surgery Using Retrograde Cerebral Perfusion", Cardiovascular Surgery, Dec. 1993, pp. 701–703, vol. 1, No. 6.

Ueda Et Al, "Deep Hypothermic Systemic Circulatory Arrest and Continuous Retrograde Cerebral Perfusion for Surgery of Aortic Arch Aneurysm", Eur J Cardio–thorac Surg, 1992, pp. 36–41, vol. 6.

Ueda Et Al, "Protective Effect of Continuous Retrograde Cerebral Perfusion on the Brain During Deep Hypothermic Systemic Circulatory Arrest", J Card Surg, 1994, pp. 584–595, vol. 9.

Usui Et Al, "Cerebral Metabolism and Funciton During Normothermic Retrograde Cerebral Perfusion", Cardiovascular Surgery, 1993, pp. 107–112, vol. 1, No. 2.

Usui Et Al, "Comparative Experimental Study Between Retrograde Cerebral Perfusion and Circulatory Arrest", The Journal of Thoracic and Cardiovascular Surgery, 1994, pp. 1228–1236, vol. 107, No. 5.

Usui Et Al, "Retrograde Cerebral Perfusion Through A Surperior Vena Caval Cannula Protects the Brain", Ann Thorac Surg, 1992, pp. 47–53, vol. 53.

Yasuura Et Al, "Clinical Application of Total Body Retrograde Perfusion to Operation for Aortic Dissection", Ann Thorac Surg, 1992, pp. 655–658, vol. 53.

Yasuura Et Al, "Resection of aortic Aneurysms Without Aortic Clamp Technique With the Aid of Hypothermic Total Body Retrograde Perfusion", The Journal of Thoracic and Carciovascular Surgery, 1994, pp. 1237–1243, vol. 107, No. 5.

FIG. 6

| PATIENT | IRCP (ml/min) | ORCP (ml/min) | WASH-OUT (ml/min) | ERCP (%) | SRCP (%) |
|---|---|---|---|---|---|
| 1 | 310 | 138 | 172 | 44 | 56 |
| 2 | 700 | 150 | 550 | 21 | 79 |
| 3 | 360 | 95 | 265 | 26 | 74 |
| 4 | 500 | 250 | 250 | 50 | 50 |
| 5 | 235 | 135 | 100 | 57 | 43 |
| 6 | 330 | 160 | 170 | 48 | 52 |
| 7 | 200 | 100 | 100 | 50 | 50 |
| 8 | 340 | 240 | 100 | 70 | 30 |
| 9 | 275 | 60 | 215 | 22 | 78 |
| 10 | 360 | 140 | 220 | 38 | 62 |
| 11 | 490 | 340 | 150 | 69 | 31 |
| 12 | 260 | 100 | 160 | 38 | 62 |
| MEAN | 363.3 | 159 | 204.3 | 44.9 | 55.1 |
| S.D. | 139.6 | 79.7 | 122.6 | 16.3 | 16.3 |
| S.E.M. | 40.3 | 23 | 35.3 | 4.2 | 4.7 |

ABBREVIATIONS:

IRCP = RCP IN FLOW
ORCP = RCP OUT FLOW
WASH-OUT = NON-RETURNED RCP FLOW
ERCP = EFFECTIVE RCP
SRCP = SEQUESTERED RCP

FIG.7

| PATIENT | INFRA P (mmHg) | SUPRA P (mmHg) | GRAD (mmHg) | ERCP (%) | GRAD IMP (%) |
|---|---|---|---|---|---|
| 1 | 20 | 20 | NONE | 46 | NONE |
| 2 | 25 | 17 | 8 | 21 | 32 |
| 3 | 24 | 18 | 6 | 26 | 25 |
| 4 | 19 | 19 | NONE | 50 | NONE |
| 5 | 24 | 24 | NONE | 57 | NONE |
| 6 | 24 | 20 | 4 | 48 | 16.7 |
| 7 | 20 | 20 | NONE | 50 | NONE |
| 8 | 24 | 24 | NONE | 70 | NONE |
| 9 | 54 | 24 | 30 | 22 | 40.1 |
| 10 | 24 | 18 | 6 | 38 | 25 |
| 11 | 25 | 25 | NONE | 69 | NONE |
| 12 | 47 | 24 | 23 | 42 | 49 |
| MEAN | 27.5 | 21.1 | 5.8* (11.5) | 44.9 | 31.3 |
| S.D. | 11.1 | 2.9 | 8.4 (8.6) | 16.3 | 11.6 |
| S.E.M. | 3.2 | 0.8 | 2.4 (3.5) | 4.7 | 4.7 |

ABBREVIATIONS

INFRA P = INFRAVALVULAR SVC PRESSURE
SUPRA P = SUPRAVALVULAR IJV
PRESSURE GRAD = GRADIENT, i.e. INFRA P - SUPRA P
(FIGURES IN BRACKETS REPRESENT DATA FOR GROUP MANIFESTING A GRADIENT.)
ERCP = EFFECTIVE RCP (DUPLICATED FROM FIG.6)
GRAD IMP = GRADIENT IMPACT (DECREASE) ON RCP INFLOW PRESSURE
*$p<0.05$ (i.e. STATISTICAL SIGNIFICANCE)

RETROGRADE PERFUSION MONITORING AND CONTROL SYSTEM

BACKGROUND OF INVENTION

1. Field of Invention

The present invention is related to retrograde perfusion, in particular in connection with cardiopulmonary bypass, and more particularly including a dedicated retrograde cerebral perfusion apparatus with systems and apparatus to monitor and enhance the flow of blood across the brain.

2. Description of the Prior Art

Cardiopulmonary Bypass (CPB)

Cardiopulmonary bypass (CPB) enables patients to undergo cardiac or "open-heart" surgery. CPB is also termed "extracorporeal circulation" (ECC), or the "heart-lung machine." As the name implies, CPB performs the function of the heart (pumping blood) and lungs (oxygenating blood). During cardiac or open heart surgery, surgeons often need to arrest the contractile function of the heart in order to operate. During this phase, the function of the heart and lungs are taken over by a heart-lung machine, known as cardiopulmonary bypass.

There are several different arrangements for cardiopulmonary bypass, each having certain basic components. Blood is drained from the venous section (right) of the heart via a single cannula in the right atrium (atrial) or via two cannula placed in the superior and inferior vena cava (bicaval). If cannula cannot be placed for technical or anatomic reasons, the venous drainage may be accomplished via a cannula in the femoral vein (groin region). An arterial cannula is placed in the aorta and returns oxygenated blood back to the patient. This cannula usually enters the aorta above the aortic valve.

If the aorta is diseased such as by the presence of an aneurysm, the arterial line may be placed in the femoral or iliac artery instead of the aorta. Instead of a bicaval venous line, the femoral vein may be used for venous return. These arrangements are commonly termed "femoral-femoral bypass", "bicaval-femoral bypass", or "atrio-femoral" bypass.

In a simple CPB system, blood flows from a venous line through an extracorporeal circuit where it is oxygenated and pumped back to the body of the patient through an arterial line. The pump serves as the mechanism for drawing blood from the right side of the heart through the various other components of the CPB system and back to the patient via the arterial component described below. Two types of extracorporeal pumps are available, peristaltic or roller pumps, and centrifugal pumps. Peristaltic pumps compress tubing creating movement of blood. Centrifugal pumps have spinning fins that create movement of blood within tubing. Because roller pumps are more traumatic to blood elements, centrifugal pumps are often preferred.

The oxygenator adds oxygen to blood and enables removal of carbon dioxide. Blood flows through the oxygenator back to the patient. In bubble oxygenators, oxygen is bubbled through the blood, whereas in membrane oxygenators, blood is oxygenated through contact with an elaborate system of membranes or silicone fibers. Generally, membrane oxygenators are superior to bubble oxygenators and have become the standard during open-heart surgery. Oxygenators must have a gas supply in conjunction with other components including an oxygen analyzer and flowmeter. The type of oxygenator used determines the arrangement of various CPB components. When bubble oxygenators are used, the pump is typically in-line after the oxygenator. Conversely, when membrane oxygenators are used, a blood reservoir precedes the in-line pump which precedes the heat exchanger/oxygenator ensemble. This arrangement is suited to the retrograde cerebral perfusion system discussed below.

The function of the heat exchanger is to add or remove heat from blood in order to control body temperature. As described below, during cardiac surgery, surgeons may elect to cool the patient. Heat exchangers typically have a large metal surface which creates a boundary between the blood and water circulating through the heat exchanger. Because of a temperature difference between of the water and the blood, a heat transfer process permits heating or cooling of the blood.

The venous reservoir serves as a back up system for the CPB circuit. Since flows of four to five liters/minute may be needed for a large adult male, a reservoir of blood is needed to ensure that air is not pumped back to the patient. The reservoir serves as a depot of blood volume for the CPB circuit. In addition, a cardiotomy reservoir may be incorporated into the CPB circuit for collection of air and debris. The cardiotomy reservoir collects blood recovered from the surgical field or via venting. Cardiotomy blood may be quite denatured, requiring special defoamers and filters to remove clots, other large particulate debris and microemboli. In addition, several filters may be incorporated into the CPB circuit for collection of air and debris.

Various techniques are used to arrest the heart using special solutions known collectively as cardioplegia. Cardioplegia usually comprises a solution that arrests the heart so that it is not contracting during surgery and contains materials capable of protecting the heart muscle from ischemic injury during the period of arrest. Cardioplegia contains high concentrations of potassium, and may have either a blood (sanguinous) or crystalloid (asanguinous) basis. Cardioplegia may be administered either antegrade (the cardioplegia solution is passed via the aortic root into the coronary arteries) or retrograde (the flow of cardioplegia is directed via the coronary sinus and veins backwards into the coronary arteries) and may be either warmed or cooled. Retrograde cardioplegia systems, so named because the venous component of the heart is directly perfused, have their own blood reservoirs, heating circuits, and pumping mechanisms which may or may not incorporate oxygenated blood. Retrograde cardioplegia is completely different from retrograde cerebral perfusion. Retrograde cardioplegia delivery has also been termed "retroperfusion." Retroperfusion in this context refers to perfusion of the cardiac muscle itself through retrograde flow. The term "retrograde perfusion" in the context of this application refers to the pumping of oxygenated fluids in a retrograde direction into the venous vessels with or without collection of deoxygenated fluids from arterial vessels. "Retrograde cerebral perfusion" pertains to a subset of retrograde perfusion in which the brain is perfused in a direction retrograde to the direction of normal blood flow. The term "fluids" in the context of this application refers to blood, synthetic fluids, or mixtures of the two.

Systems for direct perfusion of the heart without open-chest surgical procedures have been developed for acute treatment of heart attacks using extracorporeal circulation via the femoral arteries. Such a system, as described in U.S. Pat. No. 5,011,469, is directed towards treating damaged myocardium rather than preventing or minimizing damage to the brain as is the subject of the present invention.

Theoretically, some systems designed for controlled delivery of fluids during surgery could be adapted for pumping oxygenated fluid mixtures through the brain. Thus, International Application PCT/US95/02694 is directed towards a pressure control system for delivery of cardioplegia and other blood mixtures to the heart at defined constant pressure, but suggests that the system may be adapted for use in the controlled perfusion of other isolated structures such as a limb or the brain. The reference describes the use of control panels and visual displays to provide information on pressure within the relevant aspects of the perfusion system together with pressure control and pumping means. PCT/US95/02694 does not describe the use of a pediatric scaled retrograde perfusion apparatus for use in adults. Further, PCT/US95/02694 does not contemplate or provide a solution for the special problem of internal jugular vein valve impedance encountered during retrograde perfusion of the brain that is a subject of the present invention.

Hypothermic CPB and Profound Hypothermic Circulatory Arrest

As mentioned above, during cardiopulmonary bypass, the patient's body may be cooled to 24° C. This is known as hypothermic cardiopulmonary bypass. Lowering the body temperature provides protection to certain organs such as the brain. However, some surgeons do not cool the body during CPB and proceed with normothermic CPB. Alternatively, surgeons may use a combination of techniques such as cooling of the heart but not the body.

Certain forms of cardiac surgery use hypothermic cardiopulmonary bypass in connection with another modality. With aneurysms of the aortic arch, for example, cardiopulmonary bypass is used with either Profound Hypothermic Circulatory Arrest (PHCA) (cooling to 14–19° C.) or deep hypothermic circulatory arrest (cooling to 20–25° C). The cardiopulmonary pump is then switched off so that all circulatory function ceases. During PHCA, the surgeon repairs the aneurysm as quickly as possible so that hypothermic cardiopulmonary bypass and perfusion of the brain and other vital organs may recommence. Once cardiopulmonary bypass has restarted, the patient is gradually warmed to normal body temperature, until such time as cardiopulmonary bypass may be withdrawn and normal myocardial function resumed.

PHCA should not last longer than forty-five to sixty (45–60) minutes which is considered to be the safe limit for PHCA because irreversible brain damage may ensue even at low temperatures. After about sixty minutes, the incidence of cerebrovascular accidents such as stroke increases dramatically. In spite of this risk, the time required to effect repair may exceed the 45–60 minute window of relative safety.

Cerebral Perfusion

The time limitation associated with PHCA has led researchers and clinicians to explore other techniques or at least modifications or improvements of existing techniques that will prevent damage to the brain during periods of prolonged oxygen deprivation. One such technique is called "selective/antegrade perfusion" of the cerebral vasculature. In this technique, the surgeon places additional cannula in the innominate (brachiocephalic), left common carotid, or left subclavian arteries in order to permit selective perfusion of the brain using the normal direction of vascular flow. Continuous cooling and administration of neuroprotective agents during PHCA may be additional advantages. Selective/antegrade perfusion may also be used in conjunction with systemic perfusion via the femoral artery during PHCA, with or without clamping the distal aorta (referred to as the open anastomosis technique).

Although selective/antegrade perfusion affords significant brain protection during PHCA, and is clearly better than PHCA alone from the standpoint of cerebral oxygenation, selective/antegrade perfusion is technically very cumbersome and may interfere with the surgical approach or prolong the duration of PHCA. More significantly, placement of the cannula in the carotid arteries may damage friable vessels and dislodge atheromatous material into the cerebral circulation and has been associated with a high stroke incidence. Svensson et al., *J. Thorac. Cardiovasc. Surg.* 106:19–31 (1993). Indeed, notwithstanding effective cerebral circulatory support provided by antegrade perfusion, the incidence of survival using antegrade perfusion is not significantly improved over no perfusion at all because of the dramatic increase in deaths due to stroke. Kitamura et al., *Ann. Thorac. Surg.* 59: 1195–1199 (1995).

Retrograde Cerebral Perfusion

Another technique used during PHCA is called retrograde cerebral perfusion (RCP). Like selective/antegrade perfusion, the brain is perfused during RCP but in an opposite direction to normal perfusion, i.e. via the internal jugular veins. Retrograde cerebral perfusion was first used to prevent or control the incidence of air embolism during cardiac surgery. Mills and Ochsner, *J. Thorac. Cardiovasc. Surg.* 80:708–717 (1980). Subsequently, intermittent RCP was used for the purpose of providing protection to the brain during PHCA. Lemole et al., *J. Thorac. Cardiovasc. Surg.* 83:249–255 (1982). Later, continuous retrograde cerebral perfusion was developed after surgeons noted the appearance of dark, deoxygenated blood at the aortic arch suggesting perfusion of the brain in the opposite or retrograde direction to normal circulation. Ueda et al., *J. Cardiovasc. Surg.* 31:553–558 (1990).

During continuous RCP, blood is forced to flow in the opposite direction up the internal jugular vein to the brain. If blood traveled unimpeded up this path, it would be expected to perfuse the brain, travel down the carotid arteries and be ultimately recovered at the aortic arch. The appearance of dark, deoxygenated blood at the aortic arch suggests that perfusion does in fact occur and that brain metabolism is supported although in an opposite direction to that which occurs during normal circulatory function. Ueda et al., *J. Card. Surg.* 9: 584–595 (1994). Moreover, canine research suggests that retrograde cerebral perfusion provides nutritional substrates to the brain during PHCA and washes acid metabolites out of the brain. Usui et al., *Ann. Thorac. Surg.* 53: 47–53 (1992).

Research has also shown that retrograde cerebral perfusion is effective in augmenting the brain protection provided by PHCA. By providing perfusion of the brain, retrograde cerebral perfusion has the potential to increase the safe duration of PHCA. In a recent study using hypothermic circulatory arrest alone, 3/3 patients whose surgeries exceeded 60 minutes never regained consciousness after surgery. In contrast, when RCP was used, all 16 patients whose surgery exceeded 60 minutes regained consciousness without evidence of overt neurologic sequelae. Deeb et al., *J. Thorac. & Cardiovasc. Surg.* 109: 259–268 (1995). Importantly, as compared with antegrade cerebral perfusion, retrograde cerebral perfusion has been found to be significantly easier to perform, is less demanding of the surgeon's time, requires less equipment in the surgical field, and avoids the risk of damage to vital arteries supplying the brain. Yasuura et al., *Ann. Thorac. Surg.* 53: 655–658 (1992).

While RCP holds out the promise of protecting the brain from the devastating effects of anoxia during prolonged surgery, several problems remain. It is uncertain in each individual patient whether effective blood flow to the brain is occurring because valves may be located in the internal jugular vein which may partially or completely impede flow of oxygenated blood or pharmacologic agents to the brain. Cerebral death, thought to be due to such blockage, has been reported. Tsuchida et al., Cardiovasc. Surg. 1: 701–703 (1993).

Studies have provided estimates that in over 80% of the human population, single, bicuspid or tricuspid valves exist within both internal jugular veins (IJV) approximately one inch distal (toward the head) to the junction of the IJV with the brachiocephalic/subclavian vein. These valves are thought to be vestigial remnants of a valvular system required to maintain intracranial pressure when walking in a semi-horizontal position. Conversely, in some patients, the valves may be nonexistent or poorly developed. While IJV valves are apparently not necessary, they are thought to function in limiting transmission of excessive increases in venous pressure to the brain during coughing, straining or Vasalva maneuvers. Studies have shown competence of these valves against pressure, such as during straining or coughing while controlled studies in cadavers have examined competence of these valves against pressure to retrograde flow at various pressures. In approximately 10 to 15 percent of patients, IJV valves may resist pressures as high as 75 mm Hg. Further, the competence of these valves may be influenced by monitoring lines which are placed during surgery in the internal jugular veins and resulting in reduced valve impedance.

Retrograde cerebral perfusion is currently performed by selective clamping of cannula in place for use with the cardiopulmonary bypass machine. By selective clamping of the arterial and venous lines and through use of cannula placed in the large arterial and venous vessels entering and leaving the heart, blood may be directed in a retrograde direction up the superior vena cava and the internal jugular veins by the action of the cardiopulmonary bypass pump. Numerous examples exist in the medical literature which describe the use of routine cardiopulmonary bypass equipment to drive retrograde cerebral perfusion. Examples and descriptions of the current practice of effective retrograde perfusion by selective clamping of arterial and venous lines running to the cardiopulmonary bypass machine can be seen in McLoughlin, et al., "Continuous Retrograde Cerebral Perfusion as an Adjunct to Brain Protection During Deep Hypothermic Systemic Circulatory Arrest", *J. Cardiothorac. & Vasc. Anest.* 9: 205–214 (1995); Murase et al., "Continuous Retrograde Cerebral Perfusion for Profusion of the Brain during Aortic Arch Surgery", *Eur. J. Cardiothorac. Surg.* 7:597–600 (1993); Raskin and Coselli, "Retrograde Cerebral Perfusion: Overview, Techniques and Results", *Perfusion* 10: 51–57 (1995); and Ueda et al., "Protective Effect of Continuous Retrograde Cerebral Perfusion on the Brain During Deep Hypothermic Systemic Circulatory Arrest", *J. Card. Surg.* 9: 584–595 (1994).

A synchronized gas operated balloon catheter inflation apparatus for effecting retrograde perfusion of the heart and other organs is the subject of U.S. Pat. No. 5,011,468. This reference is directed towards a retrograde perfusion and retroinfusion control apparatus that inflates and deflates balloon catheters to occlude and redirect blood flow in synchrony with the normal cardiac cycle. While the reference primarily describes the operation of a balloon catheter pumping means synchronized to electrocardiographic signals dedicated to the retrograde perfusion of the heart, it includes the possibility of using a modified system for selective retrograde perfusion of the brain by diverting balloon catheters branching from the primary cardiac oxygenation loop for retrograde perfusion of the brain. The system described in 5,011,468, if modified for cerebral retrograde perfusion, would avoid the problem of blood flow impedance caused by valves within vessels leading to the brain by placement of balloon catheters in a supravalvular position distal to the internal jugular vein valves. Thus, this reference is directed to a perfusion system that is fundamentally different from that used in the present invention.

U.S. Pat. No. 4,686,085 and related patents issued to Osterholm describe systems that deliver specialized solutions into the cerebrospinal fluid pathways for selective perfusion of the brain for treatment of ischemic incidents (stroke). The Osterholm references are completely different in methodology and purpose from the present invention because they describe perfusion through the ventriculocisternal spaces occupied by cerebral spinal fluid rather than the blood vasculature of the brain. The purpose of the Osterholm inventions is to minimize the effects of stroke rather to prevent damage to the brain during cardiovascular surgery as is the subject of the present invention.

Blood flow to the brain during retrograde cerebral perfusion, may be effected by using either selective or non-selective flow cannula. Selective flow cannulation is accomplished by placement of a cannula within the internal jugular vein. Non-selective flow cannulation describes an inflow system via the right atrium or the superior vena cava. Placement of the cannula in selective flow cannulation may be either infra or supravalvular. Infravalvular inflow means the retrograde cerebral perfusion flow is delivered below the internal jugular vein valves. Supravalvular inflow describes flow delivery above internal jugular vein valves thus solving problems of potential impedance produced by valves within the internal jugular veins. While this placement obviates concerns about valvular flow impedance, this procedure is often technically impracticable because it requires placement of occlusive cannula high in the cervical region. Furthermore, anesthesiologists routinely place catheters in the internal jugular vein to monitor central venous pressure, which may interfere with cannula placement using the selective method. Thus, while supravalvular selective flow systems solve the problems of possible flow impedance with the internal jugular vein valves, they involve significant difficulties in achieving the placement of the cannula and may damage the internal jugular vein valves.

RCP effected using a non-selective infravalvular system avoids problems with cannula placement and is a subject of the present invention. The present invention describes an apparatus in which inflow conduits, typically employing cannula, are placed infravalvular, or on the heart side, of the internal jugular vein valves. This placement is herein described as "proximal" to the location of the internal jugular vein valves. Flow measurement means, such as pressure manometers, are placed in association with the inflow conduits in order to insure that desired input pressures are met but not exceeded.

The resistance to sustained flow and pressure is slightly different physiologically from that occurring with a sudden increase in pressure (such as with coughing). In the former, valves have been observed to flutter so that impedance is not complete but instead, partial. With partial obstruction, some blood flow does occur across the valves. Nonetheless, when retrograde cerebral perfusion is initiated, these valves may produce variable and unpredictable impedance to blood flow up the internal jugular veins. Valve impedance can increase the rate of shunting into collateral venous systems such as into the azygos venous system.

The azygos vein originates from the SVC prior to its bifurcation into the brachiocephalic veins. The azygos vein runs down through the thoracic and lumbar region branching extensively along the way to create the "caval-azygo-lumbar" venous system. One of these branches connects to the vertebral venous system which contributes to venous plexi of the foramen magnum which is in turn connected to the intracranial venous sinuses. Thus, the azygos system provides another potential avenue to deliver blood and pharmacologic agents to the brain.

Ultimately, the azygos vein drains into the inferior vena cava. A cadaveric study using latex infusion has indicated that, during RCP, pressure induced by valvular obstruction of the internal jugular vein forces additional blood into the azygos vein. In the face of near complete valvular obstruction, the azygos system may provide a major conduit of retrograde fluids into the central nervous system. De Brux et al., *Ann. Thorac. Surg.* 60:1294–1298 (1995). Animal evidence has suggested that some, if not a majority of the blood introduced in a retrograde fashion into the internal jugular vein flow is diverted into the azygos vein. From there it could flow either down into the inferior vena cava or to the brain by a route different than through the internal jugular vein. Questions still remain as to percentage of blood which is actually shunted through channels other than the cerebral vasculature. Although blood recovered from the retrograde stream appears to be deoxygenated, it is possible that the oxygen has been absorbed in tissues other than the brain, i.e. muscle bone, skin, etc.

Taken together, it is clear that variability between individuals in the resistance of the internal jugular vein valve to retrograde flow, and the associated shutting to collateral vessels, results in the observed lack of direct, predictable correlation between perfusion pressure and perfusion flow rates. For these reasons, maintenance of desired perfusion pressure at the level of the superior vena cava and even maintenance of desired flow rates therein may not provide accurate estimates of cerebral perfusion. Thus, surgery may be continued beyond the safe period of 45–60 minutes under the mistaken impression that the brain is safe from anoxic damage and it is only upon failure of attempted resuscitation after completion of the procedure that insufficient oxygenation is retrospectively discovered.

Because problems with internal jugular vein valve impedance may result in occult failure of cerebral oxygenation, effective retrograde cerebral perfusion using non-selective infravalvular flow cannulation requires improved systems for monitoring and controlling blood flow to the brain. A need exists for a dedicated system that selectively treats retrograde cerebral perfusion as an independent circulation, as opposed to the current practice of providing RCP using modifications of standard extracorporeal circuit or cardiopulmonary bypass equipment. Such a dedicated system could provide oxygenation and cooling of blood in a controlled manner as well as to provide improved and more isolated perfusion of the brain with desired pharmacologic agents.

There is a need for a system designed specifically for retrograde perfusion which is controlled independently from the cardiopulmonary bypass machine and is designed for the flow rates used during retrograde perfusion. The cardiopulmonary bypass apparatus is capable of flow rates of up to 5 liters per minute. Retrograde perfusion is typically conducted at flow rates of less than 600 milliliters per minute. The lower flow rates required by retrograde perfusion could be more effectively provided using smaller scale apparatus that is designed for lower flow rates. Equipment, including pumps, oxygenators, and heat exchangers currently available for use in pediatric surgery are better suited to retrograde perfusion. Smaller scale equipment provides for reduced prime volumes and conserves both the patient's blood, synthetic fluid mixtures and pharmacologic additives. In the context of this application, pediatric scale refers to perfusion equipment with maximum flow rates of less than 2 liters per minute. Such a dedicated system could be used not only for the retrograde perfusion of the cerebrum but could also be used if desired for perfusion of an isolated organ or organ system including the visceral organs.

There is a specific need for a system capable of determining the extent to which flow of oxygenated blood and pharmacologic agents is compromised by competent valves within the internal jugular veins. Relevant information can be acquired by concomitant monitoring of pressure both proximal and distal to the internal jugular vein valves, thus permitting estimates of the efficacy of cerebral perfusion. There is a further need for a system capable modulating pressure and thus perfusion rates within the cerebral circulation by controlling outflow via collateral circulatory pathways such as the azygos vein complex. These needs and the solution thereto form the basis of the present claimed invention.

The present invention comprises dedicated apparatus and methods for providing improved retrograde perfusion, particularly retrograde cerebral perfusion, under controlled conditions. Both the retrograde perfusion circuitry and monitoring and control apparatus are designed to be assembled from commercially available components.

SUMMARY OF THE INVENTION

The invention disclosed herein comprises both apparatus and methods dedicated to the performance of retrograde perfusion, and in particular, retrograde cerebral perfusion during cardiopulmonary bypass operations.

In a preferred embodiment, a dedicated apparatus designed for use in adults utilizes a pediatric scaled oxygenator, heat exchanger, and pump to accommodate the relatively low flow rates, typically less than 1 liter per minute, used for retrograde perfusion. The term "pediatric scaled" as used herein refers to equipment having maximum flow rates of less than 2 liters per minute of fluid. It is preferred but not necessary to the invention that other system components such as the fluid reservoir be of pediatric scale. Pediatric scaled blood filters are likewise preferred but may not be required.

The term "dedicated" as used herein refers to an integral unit comprised of at least an oxygenator, heat exchanger, pump and reservoir which are separate, and operated independently, from the cardiopulmonary bypass unit. The apparatus can be used for the perfusion of an isolated organ, such as the brain, or organ system such as the complex of visceral organs. Access to the organ or organ system is obtained by placement of an inflow conduit, typically a cannula, into a major venous vessel leading from the organ or organ system. If desired, a complete circuit may be produced by collection of post-perfusion fluid via an outflow conduit, typically a suction cannula, placed in a major arterial vessel leading from the perfused organ or organ system. "Fluid" in the context of the present invention pertains to blood, synthetic and pharmacologic compositions and combinations thereof.

In a preferred embodiment, the inflow conduit is placed in the superior vena cava in order to achieve retrograde perfusion of the cerebrum. If a complete circuit is desired, an outflow conduit is placed in the aortic arch in order to collect post-perfusion fluids flowing out of the cerebrum. Outflow fluids are pumped into the oxygenation and heat exchange circuit for treatment and recirculation. If desired, pharmacologic agents can be introduced into this perfusion circuit.

In a preferred embodiment, apparatus for retrograde cerebral perfusion using infravalvular non-selective inflow conduit placement, typically in the superior vena cava, includes at least a first flow monitoring line proximal to valves within the internal jugular veins and a second flow monitoring line, distal to such valves. "Proximal" refers to placement on the heart side of valves within the internal jugular veins while "distal" refers to placement on the head side of such valves. Flow monitoring across the internal jugular vein valves permits an estimate of perfusion efficacy. The invention anticipates that these perfusion efficacy estimates permit the surgical team to be aware that cerebral perfusion may not be sufficient to prevent damaging or life threatening complications. Flow monitoring may be performed by measuring pressure or other equivalent means of detecting flow such that flow impedance by competent valves within the internal jugular veins can be detected. Where flow impedance is detected, indicating a compromise of the desired rates of cerebral perfusion, various ameliorative measures can be taken. The rate of infusion or the concentration of pharmacologic agents can be modulated in proportion to detected variations in perfusion rates.

The invention discloses apparatus and methods for improving the perfusion of the cerebrum by occluding the inferior vena cava below its junction with the azygos vein. Such occlusion may redirect flow shunted down the azygos up to the vertebral venous system for perfusion of the cerebrum. In a preferred embodiment, occlusion is effected by inflation of a balloon catheter which is introduced via a femoral vein. The catheter can be inflated or deflated as desired in response to measured degrees of obstruction to flow into the cerebrum. The apparatus and methods for estimating rates of cerebral perfusion and compensating via an occlusive means placed in the inferior vena cava may be used with conventional retrograde perfusion apparatus, including use of the cardiopulmonary bypass unit to effect retrograde perfusion, as well as with the dedicated pediatric scale apparatus described as a preferred embodiment.

In a method of the preferred embodiment, retrograde perfusion of adult patients is performed using pediatric scaled equipment dedicated to retrograde perfusion and operated separately and independently from the main cardiopulmonary bypass unit. Retrograde perfusion using dedicated pediatric scaled equipment can be performed on either an isolated organ such as the brain or an entire organ system such as the visceral organs.

In a method of the preferred embodiment, retrograde cerebral perfusion is effected using a infravalvular non-selective inflow conduit placement. A first fluid flow monitoring means is placed on or near the retrograde cerebral perfusion inflow conduit. A second flow monitoring means is placed in the internal jugular vein distal to valves within the internal jugular vein. Indicia of flow across the internal jugular vein valves is obtained by comparing the signals produced by the first and second flow monitoring lines. Where flow measurements indicate compromise of cerebral perfusion due to blockage by competent valves within the internal jugular veins, ameliorative measures can be taken. These include modifying the rate of infusion of pharmacologic agents, increasing perfusion of the cerebrum by placing back pressure on the azygos vein system, and, if necessary, modifying the duration of the surgical procedure.

In a preferred embodiment, back pressure is placed on the azygos system via an occlusive means placed in the inferior vena cava distal to its junction with the azygos vein. "Distal" in relation to placement of an occlusive means in the inferior vena cava means on the side that is furthest from the heart. The preferred embodiment utilizes a balloon catheter threaded into the desired location via a insertion into the femoral vein in the inguinal region. Inflation or deflation of the balloon catheter can be effected in response to estimates of cerebral perfusion provided by the flow monitoring lines placed proximal and distal to valves within the internal jugular veins.

BRIEF DESCRIPTION OF THE DRAWINGS

A better understanding of the present invention can be obtained from the detailed description of exemplary embodiments set forth below, to be considered in conjunction with the attached drawings, in which:

FIG. 6 shows the measured RCP flow characteristics described in the Example.

FIG. 7 shows the RCP pressure measurement data described in the Example.

DETAILED DESCRIPTION OF THE PREFERRED EMBODIMENTS

The subject invention comprises dedicated apparatus and methodologies for retrograde perfusion. The subject invention contemplates perfusion of an isolated organ or organ system of an adult human using a dedicated apparatus including at least one pediatric scale oxygenator and heat exchanger. The subject invention also includes fluid (blood) filters, reservoirs and centrifugal pumps which may be of pediatric scale if desired. Pediatric scale is preferred as to these components due to their smaller internal volume. In the preferred embodiment, centrifugal pumps are used. If roller pumps are used, pediatric scale is probably not implicated because the only volume sequestered by roller pumps is that within the tubing. Pediatric scale is defined as having a maximum flow rate of approximately 2 liters per minute.

The input conduit of the subject invention may be placed in any major venous vessel leading from a target organ, organ system, or limb. The target organ, organ system, or limb may be perfused either with or without subsequent collection from arterial vessels leading therefrom. Where the perfusate, defined as any fluid or blood/fluid mixture used for perfusion, is collected in an outflow conduit placed within an arterial vessel leading from the perfused organ, treated by oxygenation, filtration and heat exchange, and returned via the venous inflow conduit, a complete retrograde perfusion circuit is formed. The RCP apparatus described herein for retrograde cerebral perfusion would be substantially identical when used for perfusion of other organs or organ systems, the major differences being in the location of the inflow and outflow conduits.

In a preferred embodiment, the subject apparatus comprises a dedicated retrograde cerebral perfusion circuit, as well as improved methods and apparatus for monitoring and controlling the flow of blood across the brain during retrograde cerebral perfusion. The cerebral perfusion apparatus is preferably assembled from commercially available pediatric instrumentation because the small size and flow rates of pediatric pumps, oxygenators, heat exchangers, filters and reservoirs are better suited to the relatively low flow rates used in retrograde perfusion generally and to the circulatory volume of the cranial compartment in particular.

Figure 2:
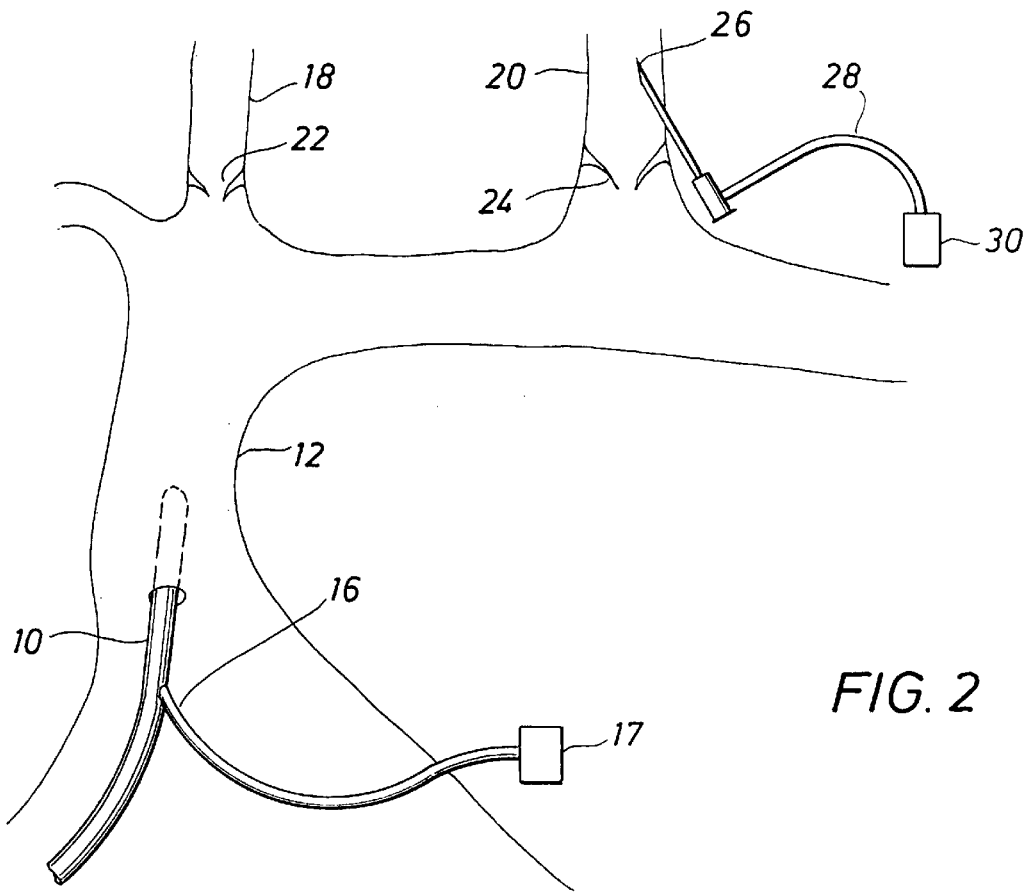
FIG. 2 is a schematic view of the monitoring system of the subject invention showing distal and proximal flow monitoring lines.

As shown in FIG. 2, for the infravalvular, nonselective approach, a RCP inflow cannula 10 is placed in the superior vena cava 12 (and is probably already in place as part of the bicaval cardiopulmonary bypass. When retrograde cerebral perfusion commences, the venous return line of the cardiopulmonary bypass circuit 41 and the inferior vena cava cannula are clamped to ensure that flow preferentially flows up the superior vena cava into the internal jugular vein.

Figure 1:
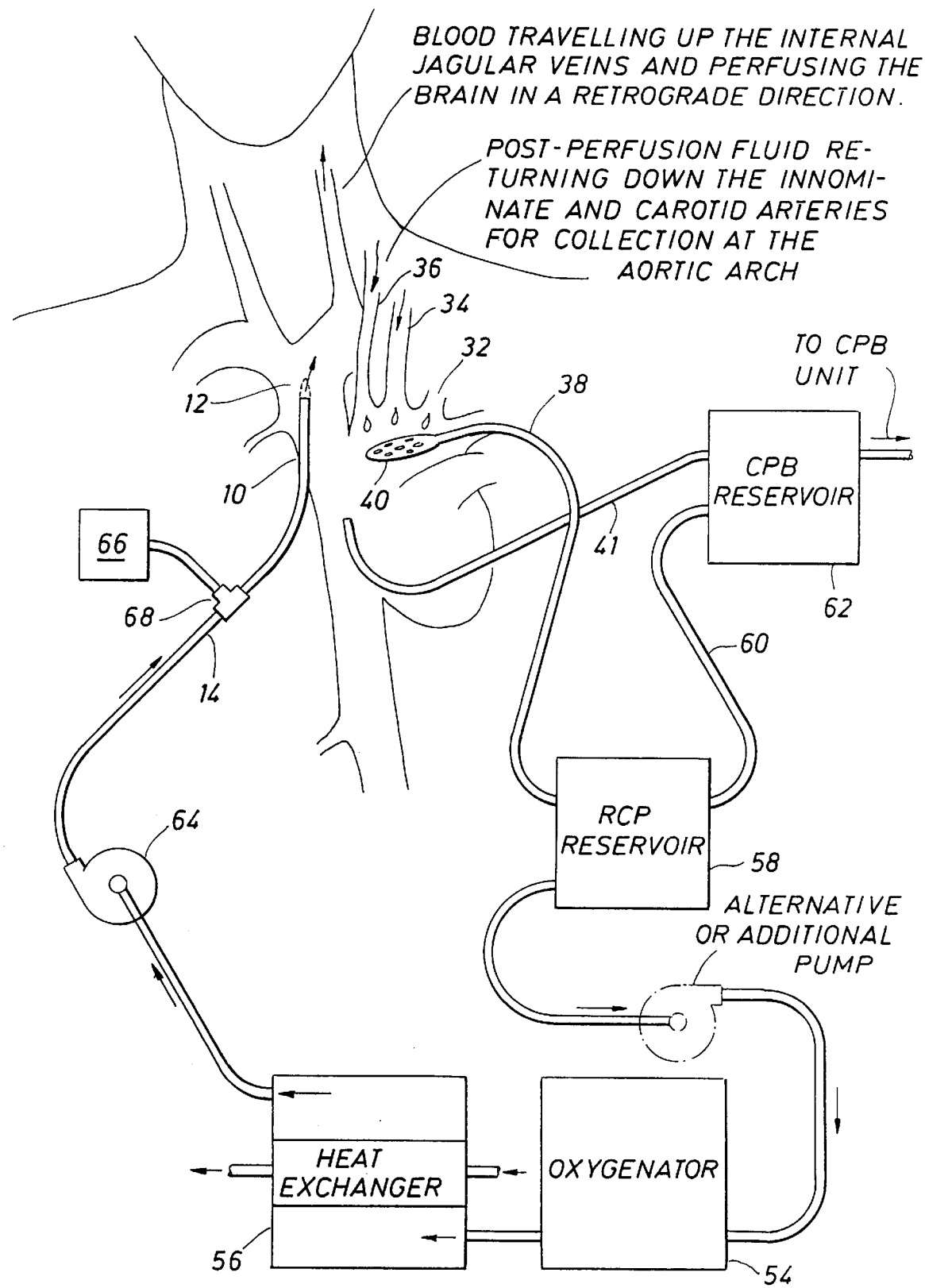
FIG. 1 is a schematic view of the dedicated retrograde cerebral perfusion circuit of the subject invention together with suggested connection to the main CPB unit.

As shown in FIG. 1, during retrograde cerebral perfusion, fluid introduced via an inflow conduit in the superior vena cava travels up the internal jugular vein, perfuses the brain, and returns via the innominate 36 and left carotid 34 arteries into the aortic arch 32. The blood is usually desaturated, indicative of oxygen uptake by brain tissues (and other tissues of the head, face and neck, such as muscle, bone and skin). Blood that appears at the aortic arch vessels is collected in accordance with the present invention via suction 40 into tubing 38 that is then directed back to a RCP blood reservoir 58 via a special port within the reservoir, to be reinfused after reoxygenation and heat exchange via the retrograde cerebral perfusion inflow tubing.

Retrograde cerebral perfusion outflow is anticipated to be less than retrograde cerebral perfusion inflow. As shown on FIG. 4, internal jugular vein valvular impedance may divert blood flow via the azygos vein 44 into the inferior vena cava 46. In addition, blood flow within the cranium may actually "shunt" past cerebral tissue and flow into other arterial structures. Therefore, the retrograde cerebral perfusion blood flow reservoir volume may need "topping up" periodically in order to support retrograde cerebral perfusion inflow. For example, consider a patient with retrograde cerebral perfusion blood flow of 300 ml/min (milliliter per minute), the RCP blood reservoir volume of 1200 ml and retrograde cerebral perfusion outflow of 50% of inflow. If the blood reservoir is not "topped up", it will empty in approximately six (6) minutes. Once empty, an extremely dangerous situation may ensure, since air may enter the system and create the potential for air embolism. Thus, as shown on FIG. 1, the present invention contemplates a connection 60 between the dedicated cerebral retrograde perfusion system and the CPB fluid reservoir 62 of the conventional extracorporeal (cardiopulmonary bypass) circuit equipment.

Cannulae and tubing are all made of medical grade polyvinyl chloride (PVC) plastic. Some modifications of PVC are being developed to reduce spallation (release of particulate material). Other types of plastic include polyethylene and ethylvinyl-acetate. Either ¼ or ½ inch internal diameter (I.D.) will be used on all tubing. Tubing size should enable flow of blood without resistance sufficient to create pressure build-up. Since flows within the RCP system are only 250–750 ml/min, ¼ or ½ inch I.D. tubing should be sufficient.

As shown in FIG. 1, the dedicated retrograde cerebral perfusion circuit of the subject invention includes a pump 64, a customized blood reservoir 58, an oxygenator 54, and a heat exchanger 56. The pump 64 should be designed to achieve flows from 200 to 750 milliliters per minute. Currently, two different types of pediatric pumps, a centrifugal and a roller pump, are commercially available. The centrifugal pump is preferred since it produces less damage to cellular elements of the blood. The pump utilized with the present invention may also incorporate a device to add pulsatility to the flow characteristics (sinusoidal waveform) as this particular characteristic augments retrograde cerebral perfusion. An example of such pump is the Model BP-50 Pediatric Bio-Pump by Medtronic, Inc. (Minneapolis, Minn.). This pump has a maximum flow rate of 1.5 liters per minute. Medtronic, Inc. also have other centrifugal pumps available including the Biomedicus Model BP 80 or Model BP 50 suited to higher flows. Another centrifugal pump is the Sarns Delphin by 3M Sarns Healthcare, Ann Arbor, Mich. Additional pumps may be required and their placement in the circuit is probably not critical to the invention.

Although more traumatic to blood elements, roller pumps may also be utilized. Examples include the 3M Sarns 9000 Universal Roller Pump or 3M Sarns Modular Perfusion System Roller Pump and the Model 043600000 Precision Blood Pump by Cobe Laboratories, Denver, Colo.

As also shown in FIG. 1, a customized RCP fluid reservoir 58 is used to support retrograde cerebral perfusion. In the preferred embodiment the reservoir has an approximate volume of 1000 milliliters. The fluid reservoir 58 is used to supply blood and or blood/fluid mixtures via the pump and along the retrograde cerebral perfusion inflow conduit tubing 14. The term "fluid" in the context of this application pertains to blood, synthetic blood compositions, and/or fluid mixtures comprising pharmacologic compounds and formulations. Fluid mixtures including pharmacologic compounds may be added to the perfusion circuit for example via a port 68 in quantities measured by metering device 66. Reservoir 58 contains two additional ports. One receives RCP outflow fluid collected by a suction element 40 and transported along a suction line 38 into the RCP reservoir 58. A suction element 40 is placed as the aortic arch 32 which receives return blood via the innominate artery 36 and the carotid artery 34 (together collectively known as RCP outflow). The second port in the RCP reservoir 58 is a fluid connection to the main extracorporeal (cardiopulmonary bypass) circuit fluid reservoir 62. The CPB reservoir connects to the main cardiopulmonary bypass apparatus.

An oxygenator 54 oxygenates or saturates blood with oxygen. Currently there are two types of available pediatric oxygenators: membrane and bubble oxygenators. However, any device known to saturate the blood with oxygen would be a suitable alternative. Examples of membrane oxygenators include the Membrane M-series Oxygenators (M2, 5, 8, 16, 30) by Jostra, USA, Austin, Tex., the ECMO Oxygenators 0600, 0800, 1500, the Affinity Hollow Fiber Oxygenator and Ultrox III Pediatric Oxygenator by Avecor Cardiovascular, Minnesota, Minn., the Minimax Plus Oxygenation Systems by Medtronic, Inc., and the Cobe VPCML made by Cobe, Lakewood, Colo. These oxygenators are actually designed for pediatric patients, the flow characteristics being similar to that required by the RCP system.

The function of the heat exchanger 56 is to cool the blood during the retrograde cerebral perfusion inflow. There are many known suitable types of heat exchangers known to those skilled in the art and commercially available. Examples include the Bio-Cal 370 Blood Temperature Control Module by Medtronic, Inc. Avecor Cardiovascular produce the ECMOtherm-II and BIOtherm Heat Exchangers. Jostra produce the HCU 20-600 Heater Cooler Unit, while Sarns 3M Healthcare produce the Sarns Heater/Cooler and Dual Heater/Cooler and Temperature Control Module.

Other components useful in the RCP system of the subject invention include products available from Medtronic Inc.: a Pediatric Arterial Filter, the Intersept, and the MCR 4000/4000F Cardiotomy Reservoirs. Avecor Cardiovascular has the Affinity Arterial Filter and a whole host of venous reservoirs, cannulae, connectors and tubing packs. Phoenix Custom Cannulae, Lincolnshire, England also supplies varieties of cannulae and tubing.

The subject invention provides a means for measuring the degree of obstruction of blood flow in the internal jugular vein by monitoring indicia of the severity of the flow differential (such as by monitoring the pressure differential) across the internal jugular vein valves. FIG. 2 shows the two internal jugular veins, 18 & 20, having intact intraluminal valves 22 and 24. A proximal pressure monitoring line 16 is connected to the inflow line 10 of the retrograde cerebral perfusion circuit. The proximal pressure monitoring line is connected to a proximal pressure transducer 17. "Proximal" in the context of flow measurement for retrograde cerebral perfusion means: on the side of the internal jugular vein valves closest to the heart. Conversely, "distal" in this context means: on the side of the internal jugular vein valves closest to the head. While in the preferred embodiment, flow is measured by pressure, any other device, known or equivalent, which can measure flow rates may be used at locations both proximal and distal to the internal jugular vein valves. The inflow line is usually at the level of the right atrium of the superior vena cava 12, and is proximal to the internal jugular veins 18 and 20.

Figure 3:
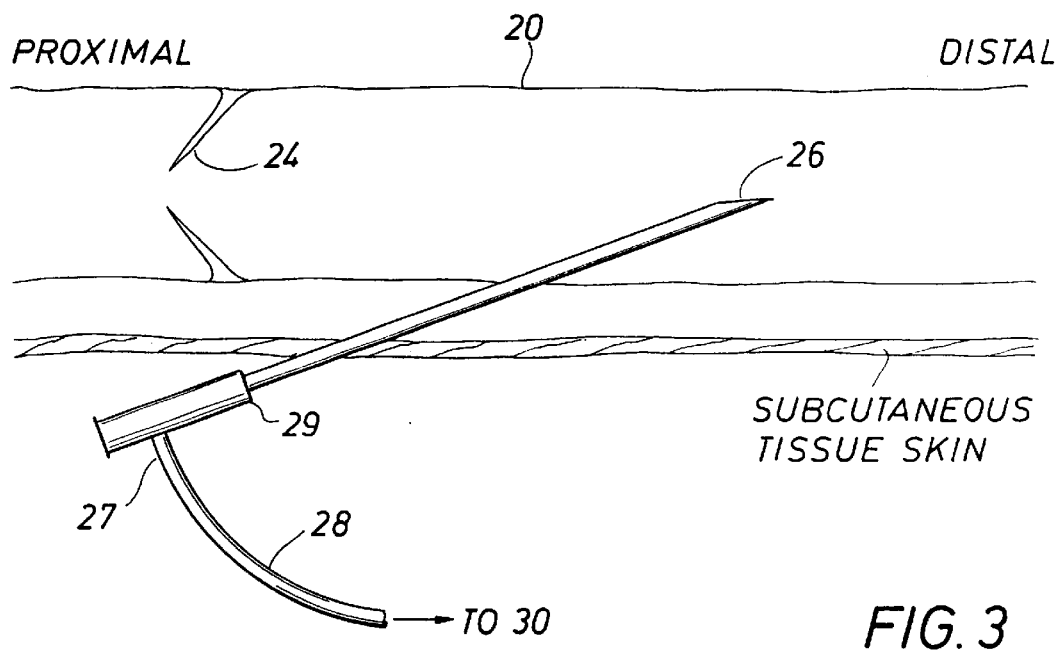
FIG. 3 is a schematic view of a pressure measurement means placed distal to an internal jugular vein valve.

In a preferred embodiment, as shown in FIG. 3, an eighteen to twenty gauge Teflon-coated catheter 26, one inch length, is placed in an internal jugular vein 20 above the valve origins, usually about one to two inches above the apex of a triangle formed by the sternal and clavicular heads of the sternomastoid muscle in the anterior neck region. Pulsation of the carotid artery is first palpated, followed by insertion of the catheter through the skin and subcutaneous tissue lateral to the artery. The catheter is directed distally into the internal jugular vein and fixed in position to ensure free flow of blood. The hub of the catheter 29 is connected to a flow monitoring line 28 via a T-connector. The distal monitoring line 28 connects to a distal pressure transducer 30. Both pressure transducers 30 and 17 should be calibrated and zeroed with reference to atmosphere. In the example below the above described system was employed and was shown to be effective in the detection of valvular impedance to blood flow.

EXAMPLE

Twelve (12) patients (Males=8, Females=4) undergoing reconstructive aortic arch surgery with PHCA and RCP were studied. Patients were placed on CPB via bicaval femoral cannula. Patients were cooled to approximately 16° C. until EEG isoelectricity was achieved. Thereafter, PHCA commenced by terminating CPB and draining cardiac blood via cannula into an extracorporeal circuit reservoir. Using Y tubing and a clamp on the venous CPB line, RCP was instituted by flowing blood via the superior vena cava (SVC) cannula, using the CPB equipment.

Methods:

RCP inflow pressure was measured at two (2) sites. The first site was monitored at the inflow line on the SVC cannula, below the expected location of the internal jugular vein valves, i.e. infravalvular. The second site consisted of a 18-g 2 inch polyethylene catheter placed in the internal jugular vein at the apex of a triangle formed by the bifurcation of the sternomastoid muscle. The catheter was directed in a cephalad direction and attached to a right-angled connector and pressure monitoring line. Therefore, this site was supravalvular in relation to the internal jugular vein valve. Pressure was monitored using traditional transducer/dome ensembles used for physiologic pressure monitoring in humans. Infravalvular and supravalvular pressures during RCP were than compared. Any difference or "pressure drop" across the valve was measured as a "pressure gradient."

During RCP, inflow rates were generally maintained between 250 and 400 ml/min, in order to maintain infravalvular inflow pressure generally at approximately 25 mm Hg. For the purpose of the experiment, venous blood from the aortic arch was carefully collected via a suction catheter placed adjacent to the origin of major arch arteries. Blood was collected in a metered reservoir which afforded measurement of outflow blood volume in order to calculate the rate of returning blood flow. For ten (10) minutes, the rates of arterial and venous RCP blood flow were recorded. In addition, following ten (10) minutes of RCP, arterial and venous blood samples were simultaneously sent for blood-gas analyses, in order to examine $O_2$ uptake or extraction and $CO_2$ production.

Results and Discussion:

All twelve (12) patients underwent surgery successfully without neurologic sequelae. The duration of PHCA was 30.7±15.6 minutes and RCP was 26.6±9.5 minutes. RCP inflow ranged 235–700 ml/min, while outflow blood ranged from 60–250 ml/min as shown in FIG. 6. In order to assess the efficacy of RCP, the proportions of blood that were either recovered or lost were compared and a ratio termed effective (E) RCP, was calculated by the following equation: Inflow RCP blood/Outflow RCP blood×100. The results suggest that only 44±16% of RCP was indeed effective in making the reverse circulatory loop through the brain. In other words, as much as 56±16% was potentially shunted to sites other than the brain. ("sequestered RCP" in FIG. 6).

Pressure measurements are shown in FIG. 7. Infravalvular SVC pressure measurements ranged from 19–54 mm Hg (mean 27.5±11.1). Supravalvular IJV pressure measurements ranged from 17–25 mm Hg (mean 21.±2.9). In six (6) of the patients no pressure gradient was detected between infra and supravalvular measurements, while in the other six (6) patients, a pressure gradient was detected. In four (4) patients, the gradient was <10 mm Hg, however, in two (2) patients, it was >20 mm Hg. Analysis of variance using the F-Test revealed f=14.43 and p<0.001 suggesting that the difference in supra and infravalvular pressure measurements did not occur by chance, i.e. they were statistically different for the whole group of twelve (12) patients. (This was verified using a paired Student's t test—i.e. t=2.23, p<0.05) When only patients manifesting a gradient are studied, i.e. we exclude the non-gradient group (n=6), the mean gradient increases from 5.8±8.4 to 11.5±8.6 mm Hg. The severity of this gradient in terms of inflow pressure is a fraction of arterial inflow where the gradient ranges from 16.7–49% (FIG. 7).

Although only six (6) out of twelve (12) (50%) patients manifested a pressure gradient, it can be seen from the data that presence of a pressure gradient was associated with lower ERCP. In other words, when a gradient was present, RCP outflow was significantly smaller than RCP inflow, suggesting that a very significant portion of the RCP inflow was sequestered or lost. Using least squares regression analysis, a correlation coefficient of −0.6 was found for RCP gradient and ERCP. In other words, 60% of the reduction in ERCP correlates with the magnitude of the pressure gradient. Analysis of blood gas data was reported in Anesth Analg 82: SCA 32, 1996.

Figure 8:
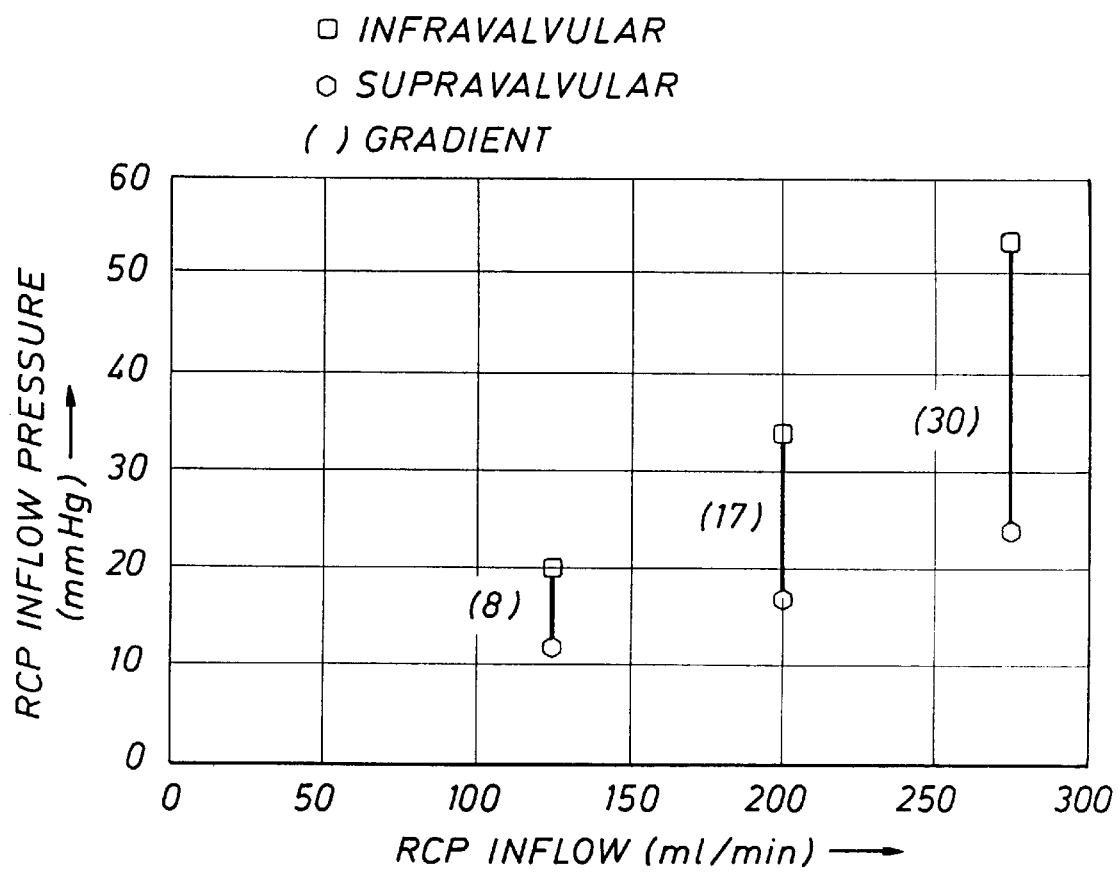
FIG. 8 shows the measured RCP pressure gradient across the IJV described in the Example.

For patient #9 above, the perfusionist attempted to increase the RCP inflow rate to attain adequate cerebral perfusion. FIG. 8 below shows that at a flow rate of 125 ml/min the pressure gradient across internal jugular vein valve was 8 mmHg. When the flow rate was increased to 275 ml/min, a 3-fold increase in flow rate, the pressure gradient rose to 30 mmHg, an almost 4 fold increase. This data suggests that IJV resistance cannot be overcome merely by increasing flow rates because resistance also increases. This observation forms part of the basis of the solution presented by the present invention. Since adequate perfusion may not be obtainable by increasing flow rates, the present invention provides a simple and relatively non-invasive solution through the occlusion of the inferior vena cava in order to place back pressure on the azygos vein system.

Summary:

RCP is able to provide some perfusion of the brain with oxygenated blood during prolonged surgery. However, not all of the RCP inflow appears in the RCP return pool. A portion is sequestered or redirected to regions other than the brain, which may be termed "washout." Possible areas of washout are veins, muscles, skin, bone of the head, etc.

IJV valves sufficient to occlude retrograde flow have been postulated to occur in 50% of individuals. The results of the present trial agree with this hypothesis. The ability of these valves to impede retrograde blood flow via the IJVs is variable and unpredictable prior to surgery. They can create significant impedance to RCP flow such that intravascular IJV flow rate and/or pressure alone is not an accurate measure of true RCP inflow. When a gradient is detected, statistically indicative of significant IJV occlusion of flow, the efficiency of RCP may decrease as a result of the likely increase in the redirection of flow via collateral circulatory paths such as the azygos vein.

While the above results substantiate the hypothesis that RCP can be an effective procedure, they also suggest that real-time measurements of IJV valve impedance using customized equipment can permit an optimized procedure. The availability of supravalvular pressure measurements provides a measure of the impedance across the IJV valves, leads to more accurate estimates of potential brain perfusion, and could be used to optimize perfusion rates by triggering the use of additional flow control procedures.

In order for RCP to be more universally effective in minimizing the risks of cerebral damage during CPB and PHCA procedures, dedicated apparatus and methodologies for monitoring IJV valvular pressure gradient are required together with procedures for reacting to the data produced by the apparatus. The above forms the basis for the development of the IJV flow, monitoring and control system herein described.

Research indicates that there are differences in valve integrity between the valves in the right and left internal jugular veins. In one autopsy study it was found that the right valve was apparently competent in 88% of cases examined while the left valve was competent in only 44% of the cases. However, in a separate angiography study, regurgitation through the right valve resulted in functional competency in the vast majority of cases. Murase et al., *Eur. J. Cardiothorac. Surg.* 7:597–600 (1993). Because these data predict anatomic and functional differences between the right and left internal jugular veins, pressure measurements on only one side may be inaccurate or misleading. Thus, as an alternative to the present preferred embodiment, pressure monitors may be placed into both right and left internal jugular veins distal to the valves. Experience may show that placement in a single internal jugular vein provides an adequate estimate of flow impedance in the vast majority of individuals obviating the need for placement of supravalvular pressure monitors in both veins.

Once retrograde cerebral perfusion commences, the optimal blood inflow is between 250 to 500 milliliters per minute, together with a proximal monitoring pressure of not more than about 25 mm Hg. Pressure is simultaneously measured in the distal pressure monitoring line. Experience indicates that, absent significant valvular obstructions, the pressures in both proximal and distal locations should be approximately equal. Presence of a pressure drop, i.e. proximal pressures higher than distal pressures, can be taken to be indicative of an internal jugular vein obstruction, suggestive of the presence of flow impeding valves. The pressure differential, also known as the internal jugular vein valvular gradient, may vary from small, i.e. 5 mm Hg, to large, i.e. 15 mm Hg. Regardless of the size, the presence of this gradient indicates that blood flow up the internal jugular vein is likely obstructed, and that optimal flow pressures of 25 mm Hg at the proximal pressure line are indeed suboptimal.

Hence, monitoring retrograde cerebral perfusion inflow pressure distal to the internal jugular vein valves provides a measure of actual retrograde cerebral perfusion. If a pressure gradient over normal is detected, flows may be increased to provide a more optimal distal, supravalvular pressure of 25 mm Hg. However, this option is only available if the impedance to flow caused by internal jugular vein valves is not very efficient such that some flow is getting through. If retrograde cerebral perfusion flows are increased and supravalvular inflow pressure cannot be increased, i.e. the gradient enlarges, than the internal jugular vein valves are indeed significantly limiting the internal jugular blood flow. The present invention includes a procedure further designed to improve this situation by pressurizing the inferior vena cava, as discussed below.

Figure 4:
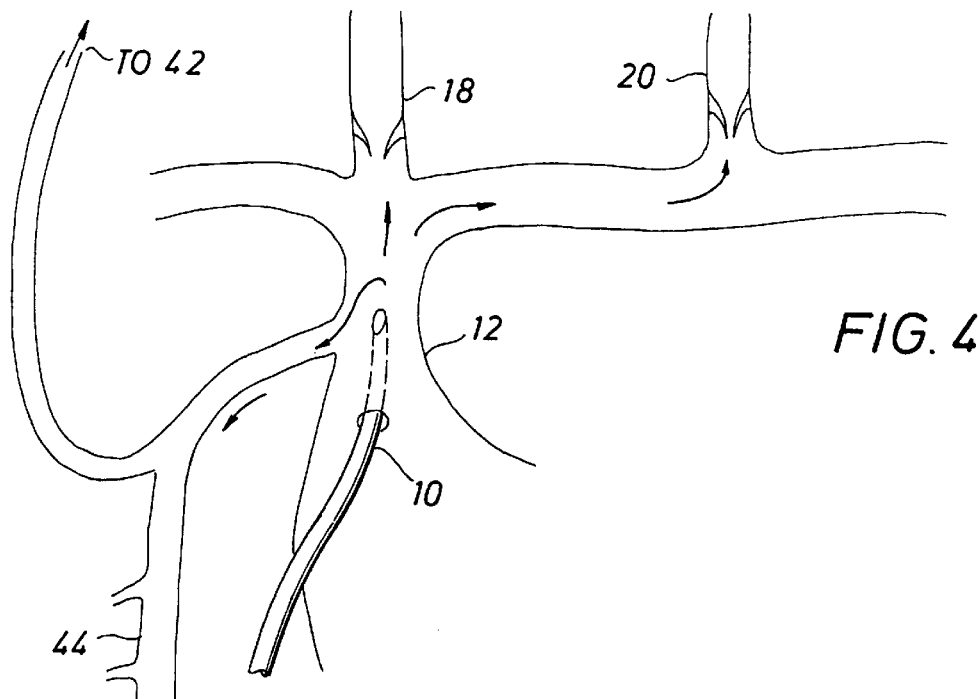
FIG. 4 is a schematic view of the possible flow paths of fluid introduced via an inflow conduit placed in the superior vena cava.

As shown in FIG. 4, the azygos vein 44 originates from the superior vena cava 12 prior to its bifurcation into the internal jugular veins 18 and 20. This vein 44 runs down to the inferior vena cava giving off several branches, known as the caval-azygo-lumbar venous system, along the way. One of the branches connects with the vertebral venous system 42. It is the vertebral venous system which contributes to venous plexi of the foramen magnum which then connects to the intracranial venous sinuses.

When valvular obstruction occurs in the internal jugular veins, various proportions of the retrograde cerebral perfusion inflow from the superior vena cava 12 are likely directed via the azygos vein 44. The larger the valvular gradient, the larger the amount of likely azygos blood flow. (The route following redirection of blood flow depends on several factors. The vertebro-azygos system serves as an alternate route to the brain during retrograde cerebral perfusion. One study has shown that when the azygos vein is ligated and there are valves in the internal jugular vein, no retrograde cerebral perfusion blood flow actually reaches the brain. Blood flow down the inferior vena cava does not participate in retrograde cerebral perfusion. Instead, perfusion of the body occurs and is known as retrograde body perfusion. When retrograde body perfusion occurs, blood flows across the abdominal venous system into the abdominal aorta and up the aorta ultimately appearing at the aortic arch, near the distal aorta, or distal aortic prosthetic anastomosis. Here, the blood is desaturated and should be suctioned back to the RCP blood reservoir. If retrograde cerebral perfusion blood flow diverts to the azygos vein 44 it is difficult to determine what proportion, if any, that flows up to the brain via the vertebro-azygos systems 42, FIG. 4, and what proportion is shunted via the inferior vena cava.)

While azygos blood flow can serve a potentially useful function during retrograde cerebral perfusion, it complicates the conceptual basis for determining adequate perfusion of the brain. In essence, variable proportions of blood flow do not flow up the internal jugular veins 18 and 20 because redirection of some retrograde cerebral perfusion blood flow via the azygos vein 44 occurs. As shown in FIG. 4, while part of the azygos blood flow can reach the brain via the vertebral venous system 42, another part will flow into the inferior vena cava 46. It is the internal jugular vein valvular gradient that likely affects what portion of retrograde cerebral perfusion is redirected to the azygos system. Furthermore, whether blood flows through the vertebral as opposed to the inferior vena cava is the determined by the pressure differential of each venous system. Comparison of the vertebral venous system with the inferior vena cava reveals that the vertebral venous system is avalvulated. In addition, since the inferior vena cava is a vessel of large diameter, pressure is probably less than in the vertebral system. In order to increase blood flow in the vertebral system, pressure must be preferentially increased in the caval system to create higher pressure and thus increased flow within the vertebral system.

Figure 5:
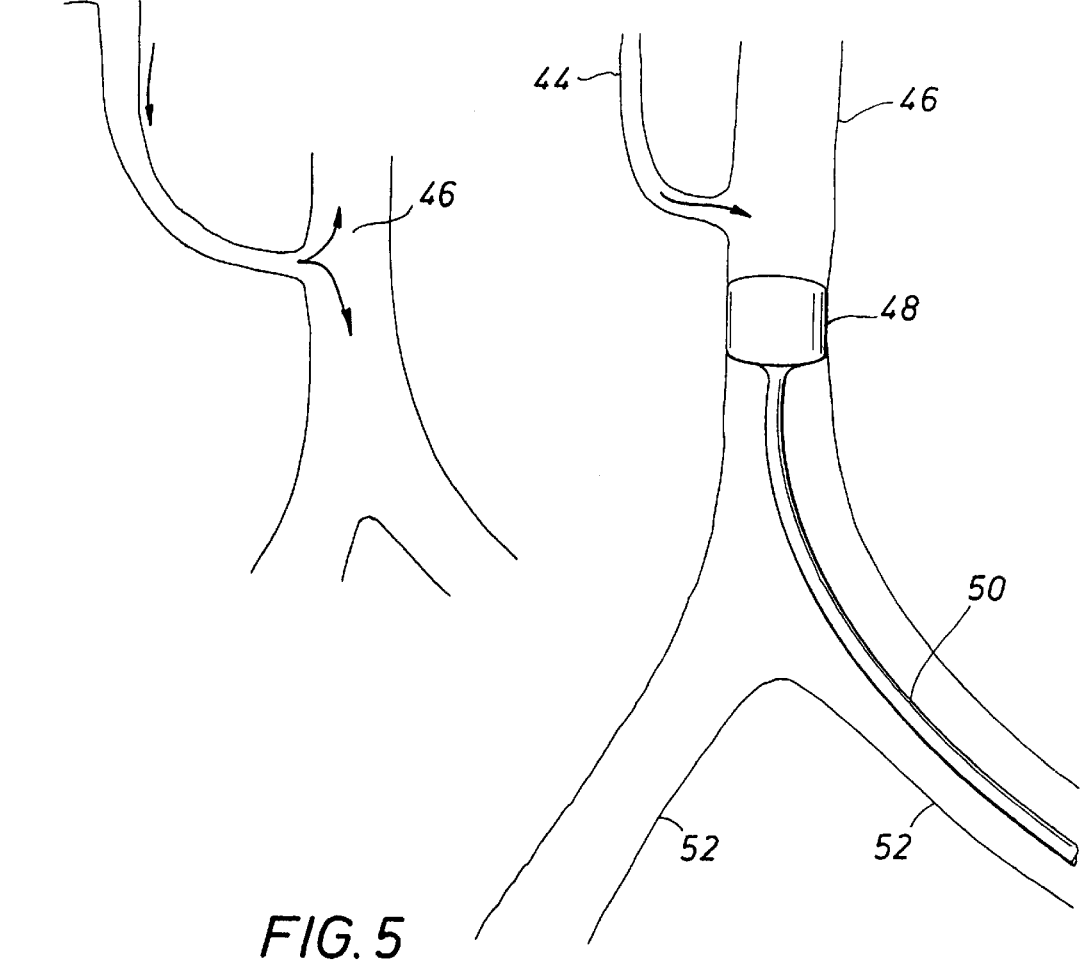
FIG. 5 is a schematic view of the use of a occlusive means in the inferior vena cava to increase perfusion of the brain during RCP.

One aspect of the method and apparatus of the subject invention involves actively increasing vertebral and ultimately cerebral blood flow by controlling the pressure in the inferior vena cava 46. As shown in FIG. 5, in a preferred embodiment, a balloon 48 is placed in the inferior vena cava 46 via the femoral vein 52 in the inguinal region. A pressure monitoring line 50 is attached. Where a significant pressure gradient across the internal jugular vein is detected, possibly indicting a compromise of the attempted perfusion of the cerebrum, the balloon 48 in the inferior vena cava 46 is inflated. This will place back pressure on the azygos vein forcing blood to flow via the vertebral system, since the pressure of the vertebral system is lower than the inferior vena cava after occlusion.

Where a pressure gradient detected by the apparatus of the subject invention indicates compromise of desired cerebral perfusion rates, measures may be required in addition to the operation of occlusive means in the inferior vena cava distal to the azygos vein junction. Such additional measures for increasing cerebral perfusion by placing backpressure on the inferior vena cava and, ultimately, the azygos system may include clamping the inferior vena cava cannula used for traditional CPB, clamping or occluding the distal aorta with a balloon, and or instituting total body perfusion by placing inflow conduit in both the superior and inferior vena cava.

As a solution to the potential problem of shunting down the azygos vein, Yasuura et al., *J. Thorac. & Cardiovasc. Surg.* 107: 1237–1243 (1994), suggested simultaneous retrograde perfusion of the abdominal viscera and the brain via inflow cannula placed in both the superior and inferior vena cava resulting effectively in total body retrograde perfusion. The present invention, in contrast, comprises methods and apparatus for evaluating the success of cerebral retrograde perfusion by measuring the flow impedance of valves within the internal jugular veins. If flow across these valves is not impeded, total body perfusion necessitating the positioning of an additional cannula is probably not necessary. Should flow impedance be detected, the apparatus and methods of the present invention effect increased pressure on the cerebral vasculature by occlusion of the inferior vena cava below its intersection with the azygos vein. In a preferred embodiment, this occlusion is effected by the simple expedient of a balloon catheter threaded up the inferior vena cava via a femoral vein in the inguinal region rather than through placement of an additional inflow cannula.

It has been reported that retrograde flow to the brain can be increased by clamping of the inferior vena cava. The present invention contemplates variably controllable occlusion rather than "clamping" and that such occlusion occurs below the entry point of the azygos into the inferior vena cava.

Retrograde cerebral perfusion system of the present invention creates a system of estimating the efficiency of delivery of pharmacological agents directly into the brain during profound hypothermic circulatory arrest. These pharmacological agents may include: 1) nutritional substrates; 2) cerebroplegics (agents which literally freeze all metabolic activity of the brain), 3) blood substitutes such as perflubron which increase the dissolved oxygen content of blood several fold; 4) anti-vasospastic substances and vasodilators which are infused to dilate the circulation and enhance blood flow; 5) oxygen free radical scavengers such as mannitol; 6) antagonists to ischemic byproducts where certain amino acids are liberated during ischemia and selective antagonists to counter or block receptors which mediate these effects; and 7) other drugs known to those skilled in the art for assisting in retrograde cerebral perfusion.

Pharmacologic agents may be administered via the inflow line of the RCP circuit. Port 68 and pharmacological source 66 of FIG. 1 indicate one structure, of many structures known and practiced in the art, for introducing pharmacological agents into a perfusion circuit. Although the actual pharmacologic agent used is not all that critical at this point, what is important is that the RCP system provides an apparatus for monitoring the administration of pharmacologic agents needed to augment neuroprotection and may provide an estimate of the extent of cerebral exposure to the administered pharmacologic agents.

Pharmacologic agents may be administered in a "bolus" injection, i.e. a single shot of agent at the commencement of RCP, either with or without a continuous infusion of agents during the duration of RCP. Since pharmacologic agents may be absorbed or adsorbed by neurological tissue following bolus injection, in order to maintain a certain blood concentration of agent within the RCP system, pharmacologic agents may need to be continuously added to the system. The rate of infusion would depend on the pharmacologic characteristics of the agent, uptake by tissue, the blood return rate to the RCP reservoir, and the extent to measured valvular impedance is thought to compromise delivery of desired levels of the agent.

Further research may indicate that the degree of RCP flow impedance at the IVJ valve is a useful measure in setting infusion rates. For example, assume that 75% of the RCP arterial flow returns to the reservoir every minute. If arterial flows were 400 ml/min, then venous return would be 300 ml/min. One might assume that the concentration of drug in the venous return line would also be 75% of the arterial concentration for the first minute and then another 75% lower for the next minute. This would lead to an exponential reduction in concentration of the agent. In this case, a continuous infusion of agent would be required to maintain therapeutic concentration of agent in blood perfusing the brain. This becomes somewhat more complicated, because uptake by tissue also influences the elimination of pharmacologic agent. Although brain metabolism is significantly reduced by hypothermia during PHCA, uptake by brain tissue may also deplete the blood concentration of pharmacologic agent, requiring incremental increase in the infusion of agent. Estimates of valve impedance allow the surgical team to titrate the administration of pharmacologic agents by increasing the relative dosage where it is apparent that a smaller percentage of the desired materials is able to perfuse the brain.

Collection of retrograde cerebral perfusion outflow enables measurements of brain injury markers during PHCA. Markers such as c-fos and S-100, both measures of neuronal injury, could guide the effectiveness of brain protection during PHCA requiring additional interventions to reverse injury if detected.

The foregoing disclosure and description of the invention are illustrative and explanatory thereof, and various changes in the size, shape, and materials, as well as in the details of the illustrated system may be made without departing from the spirit of the invention. The invention is claimed using terminology that depends upon a historic presumptive presentation that recitation of a single element covers one or more, and recitation of two elements covers two or more, and the like.

What is claimed is:

1. Apparatus dedicated to adult retrograde perfusion comprising:
    pediatric scaled perfusion equipment including at least one pump, one fluid reservoir, one pediatric-scaled oxygenator and one pediatric scaled heat exchanger, and which equipment, in combination, has a maximum flow rate of less than or equal to approximately 2 liters per minute;
    a fluid delivery inflow conduit in fluid communication with a downstream side of said pediatric-scaled perfusion equipment; and
    first means adapted and sized for establishing fluid communication between an adult-scaled venous vessel and the inflow conduit.

2. The apparatus of claim 1 wherein said apparatus includes:
    a fluid collection outflow conduit in fluid communication on the upstream side with said perfusion equipment; and
    second means adapted and sized for establishing fluid communication between an adult-scaled arterial vessel and the outflow conduit.

3. The apparatus of claim 2 wherein said first means comprises means for establishing fluid communication with a portion of an adult-scaled superior vena cava and wherein said second means comprises means for establishing fluid communication with a portion of an adult-scaled aortic arch.

4. The apparatus of claim 1 wherein said first means comprises means for establishing fluid communication with a portion of an adult-scaled superior vena cava.

5. The apparatus of claim 3 including a flow monitoring line and means for attaching said line in an adult-scaled internal jugular vein distal to an internal jugular vein valve wherein fluid passes from said inflow conduit across said internal jugular vein valve to, and past, the flow monitoring line; and
    a flow detection device connected to said monitoring line for detecting an indicia of flow across said internal jugular vein valve.

6. The apparatus of claim 5 wherein said indicia of flow includes pressure.

7. The apparatus of claim 5 that includes a second flow monitoring line and means for attaching said line in a second adult-scaled internal jugular vein distal to an internal jugular vein valve wherein fluid passes from said inflow conduit across said second internal jugular vein valve to, and past, the second flow monitoring line.

8. The apparatus of claim 5 including means attached to said apparatus for metering delivery of pharmacologic compounds.

9. The apparatus of claim 3 including means in fluid communication with said inflow conduit for occluding an adult-scaled inferior vena cava below an azygo-inferior vena cava junction.

10. The apparatus of claim 9 including means for engaging said occlusive means in response to measured indicia of flow across an internal jugular vein.

11. The apparatus of claim 10 wherein said occlusive means includes a balloon catheter.

12. The apparatus of claim 9 wherein said inclusive means includes means for communicating through a femoral vein in order to activate said occlusive means.

13. Apparatus for retrograde cerebral perfusion comprising:
    perfusion equipment;
    a fluid delivery inflow conduit in fluid communication with a downstream side of said equipment and adapted to be attached to a human venous vessel; and
    a first flow monitoring line adapted to be disposed in a human internal jugular vein distal to an internal jugular vein valve such that fluid passes from the inflow conduit across said internal jugular vein valve to, and past, the first flow monitoring line.

14. The apparatus of claim 13 including a flow detection device connected to said monitoring line for detecting an indicia of flow across said internal jugular vein valve.

15. The apparatus of claim 14 wherein said indicia of flow includes pressure.

16. The apparatus of claim 13 wherein said human venous vessel includes a superior vena cava.

17. The apparatus of claim 13 that includes a second flow monitoring line adapted to be disposed in a second internal jugular vein distal to an internal jugular vein valve within the vein such that fluid passes from the inflow conduit across said internal jugular vein valve to, and past, the second flow monitoring line.

18. The apparatus of claim 13 including means attached to said apparatus for metered delivery of pharmacologic compounds.

19. The apparatus of claim 13 including means in fluid communication with said inflow conduit for occluding an inferior vena cava below a azygo-inferior vena cava junction in response to a measured indicia of flow across an internal jugular vein.

20. The apparatus of claim 19 wherein said occlusive means includes a balloon catheter.

21. Apparatus for performing retrograde cerebral perfusion comprising:
    perfusion equipment;
    a fluid delivery inflow conduit in fluid communication with a downstream side of said equipment and adapted to be attached to a human venous vessel; and
    means, adapted for attaching to a human internal jugular vein distal to an internal jugular vein valve, for detection of an indicia of flow across an internal jugular vein valve, said means in fluid communication with said inflow conduit with communicating fluid passing from the inflow conduit across the internal jugular vein valve to, and past, the means for detection.

22. The apparatus of claim 21 wherein said flow indicia detection means comprises;
- a first flow detection means for detecting fluid flow, sized and structured for locating proximal to an internal jugular vein valve; and
- a second flow detection means for detecting fluid flow, sized and structured for locating distal to an internal jugular vein valve.

23. The apparatus of claim 21 wherein said retrograde cerebral perfusion apparatus has a maximum flow rate of less than or equal to approximately 2 liters per minute.

24. The apparatus of claim 21 including means in fluid communication with said inflow conduit for occluding an inferior vena cava of a human, said means for occluding including an occluding element sized and structured for attaching distal to a junction of an azygos vein with an inferior vena cava.

* * * * *